United States Patent
Krishnan et al.

(10) Patent No.: US 6,213,951 B1
(45) Date of Patent: Apr. 10, 2001

(54) MEDICAL DIAGNOSTIC ULTRASOUND METHOD AND SYSTEM FOR CONTRAST SPECIFIC FREQUENCY IMAGING

(75) Inventors: Sriram Krishnan; Edward A. Gardner, both of San Jose; Gregory L Holley, Mountain View, all of CA (US)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 09/253,089

(22) Filed: Feb. 19, 1999

(51) Int. Cl.[7] .................................................. A61B 8/14
(52) U.S. Cl. ............................................................ 600/458
(58) Field of Search ................................... 600/453, 455, 600/458, 447; 367/7, 11, 138; 73/625, 626

(56) References Cited

U.S. PATENT DOCUMENTS

| | | |
|---|---|---|
| 5,410,516 | 4/1995 | Uhlendorf . |
| 5,456,257 | 10/1995 | Johnson . |
| 5,632,277 | 5/1997 | Chapman . |
| 5,706,819 | 1/1998 | Hwang . |
| 5,724,976 | 3/1998 | Mine . |
| 5,733,527 | 3/1998 | Schutt . |
| 5,740,128 | 4/1998 | Hossack et al. . |
| 5,833,613 | 11/1998 | Averkiou . |
| 5,883,614 | * 11/1998 | Dodd et al. ............................. 600/447 |
| 6,050,947 | * 4/2000 | Rhyne et al. .......................... 600/447 |

OTHER PUBLICATIONS

"Simulated Capillary Blood Measurement Using a Nonlinear Ultrasonic Contrast Agent," Schrope et al.; Ultrasonic Imaging, vol. 14, pp. 134–158, 1992.

"Harmonic Power Mode Doppler Using Microbubble Contrast Agents: An Improved Method for Small Vessel Flow Imaging," Burns et al., 1994 IEEE Ultrasonic Symposium, pp. 1547–1550, 1994.

"Pulse Inversion Doppler: A New Method for Detecting Nonlinear Echoes from Microbubble Contrast Agents," Simpson and Burns, 1997 IEEE Ultrasonic Symposium, 1997.

* cited by examiner

Primary Examiner—Marvin M. Lateef
Assistant Examiner—Ali M. Imam
(74) Attorney, Agent, or Firm—Brinks Hofer Gilson & Lione

(57) ABSTRACT

A medical diagnostic ultrasound imaging method and system insonify a tissue containing a contrast agent with ultrasonic transmit signals at a fundamental frequency f. Backscattered ultrasonic receive signals are acquired and filtered to emphasize frequency components between the fundamental frequency f and the second harmonic frequency 2f, and the filtered receive signals are processed for display. This filtering enhances the ability of the method and system to discriminate between contrast agent and adjacent tissue.

22 Claims, 4 Drawing Sheets

MEDICAL DIAGNOSTIC ULTRASOUND METHOD AND SYSTEM FOR CONTRAST SPECIFIC FREQUENCY IMAGING

BACKGROUND

This invention relates to medical diagnostic ultrasound imaging, and in particular to methods and systems for distinguishing contrast agent from surrounding tissue.

Contrast agent imaging is an important medical diagnostic ultrasound imaging mode. One limitation in many contrast imaging systems is the difficulty of distinguishing echo signals from contrast agents from echo signals from surrounding tissue. This is because both contrast agents and tissue generate nonlinear return signals at frequencies other than the frequency of the insonifying signals. It is well recognized that nonlinear signals from tissue are generated by nonlinear propagation of the insonifying ultrasound wave.

Prior-art harmonic imaging methods include B-mode harmonic imaging, B-mode harmonic pulse inversion imaging, harmonic power Doppler imaging, and color harmonic pulse inversion imaging.

In B-mode harmonic imaging, the signal is transmitted at a fundamental frequency f, and the receive signal is filtered to emphasize frequency components near the second harmonic, 2f. Contrast agents are known to have a stronger second harmonic response than tissue, and for this reason the receive signal from contrast agent is enhanced over that from tissue. This method is currently used by most major manufacturers of ultrasound imaging equipment. Specific examples are described in Mine U.S. Pat. No. 5,724,976, Uhlendorf U.S. Pat. No. 5,410,516, Schutt U.S. Pat. No. 5,733,527, and "Simulated Capillary Blood Measurement Using a Nonlinear Ultrasonic Contrast Agent," Schrope et al.; Ultrasonic Imaging, Vol. 14, pp. 134–158, 1992.

In B-mode harmonic pulse inversion imaging, two pulses are transmitted along the same ultrasound line, where one pulse is shifted by 180° with respect to the other. Receive signals from the two pulses are then summed, and the resultant signal is displayed. Pulse inversion cancels stationary fundamental frequency signals and retains second harmonic signals as well as some nonstationary fundamental signals. Examples of such methods include Chapman U.S. Pat. No. 5,632,277 and Hwang U.S. Pat. No. 5,706,819.

In harmonic power Doppler imaging, multiple pulses are transmitted along the same ultrasound line, and the receive signal is filtered about the second harmonic frequency. The resultant signals are then filtered with a high-pass filter to remove stationary signals. Examples of such methods are described in Averkiou U.S. Pat. No. 5,833,613, Johnson U.S. Pat. No. 5,456,257, and "Harmonic Power Mode Doppler Using Microbubble Contrast Agents: An Improved Method for Small Vessel Flow Imaging," Burns, et al., 1994 IEEE Ultrasonic Symposium, pp. 1547–1550, 1994.

In color harmonic pulse inversion imaging, the approach used is similar to that used in harmonic power Doppler imaging described above, but alternate pulses are shifted in phase by 180°. Such methods are described in "Pulse Inversion Doppler: A New Method for Detecting Nonlinear Echoes from Microbubble Contrast Agents," Simpson and Burns, 1997 IEEE Ultrasonic Symposium, 1997.

Though these techniques succeed in presenting contrast agent enhanced images, they do not entire meet the needs of clinicians in the field. B-mode harmonic imaging does not differentiate between second harmonic signals generated by nonlinear propagation through tissue and second harmonic signals generated by contrast agents. Pulse inversion imaging further enhances second harmonic signals, but it still does not differentiate between second harmonic signals generated by nonlinear propagation through tissue and second harmonic signals generated by contrast agents. Harmonic power Doppler imaging attempts to differentiate contrast agent from tissue by looking for a loss of correlation between successive pulses due to agent destruction, agent motion or other methods. However, tissue motion will also result in a loss of correlation and may appear as a displayed signal. Tissue motion is reduced currently by a combination of increasing the pulse repetition frequency and/or the use of more aggressive clutter filters. However, increasing the pulse repetition frequency may reduce the signal from destroyed contrast agent, and more aggressive clutter filters may filter out contrast signal as well as tissue signal. These problems and drawbacks apply also to color harmonic pulse inversion techniques.

It would be advantageous to improve the specificity for imaging contrast agent as opposed to tissue. Increased specificity would allow contrast agent to be used for sensitive qualitative and quantitative measurements of blood flow in tissue.

SUMMARY

The present inventors have discovered that in the presence of medium to high power ultrasound signals, contrast agents act as highly nonlinear scatters having unique backscatter characteristics. For example, one property of this nonlinearity is that the frequency spectrum of second harmonic backscatter due to contrast agent broadens as compared to second harmonic backscatter due to nonlinear propagation of the ultrasound wave through tissue. As described below, this broadening can be used to improve the specificity of contrast agent imaging over tissue harmonic imaging. The preferred embodiments described below enhance the signal from contrast agents relative to the signal from surrounding tissue by exploiting the unique backscatter characteristics of contrast agents relative to surrounding tissue.

The present invention is defined by the following claims. The foregoing paragraph has been provided merely by way of introduction, and is not intended to limit the scope of these claims.

DETAILED DESCRIPTION OF THE PRESENTLY PREFERRED EMBODIMENTS

General Discussion

The preferred embodiments described below exploit the fact that when contrast agents are subjected to medium to high power ultrasound pulses (i.e., ultrasound pulses that provide transmit pressures of at least about 100 kPa at the transmit focus), the frequency spectrum of the second harmonic signal generated by the contrast agents broadens. This broadening is due to the inherent nonlinearity of contrast agents. Harmonic signals generated by nonlinear propagation of the ultrasound signal through tissue do not exhibit similar spectral broadening. The embodiments described below exploit these differences to improve the differentiation of contrast agent from tissue by filtering the receive signal with a receive filter that is centered between the harmonic and fundamental frequencies. Preferably, this filter can also be used to filter out both fundamental and harmonic frequencies of the receive signal such that only those frequencies between the fundamental and harmonic frequencies are passed. This approach can be used for many imaging modes, as for example B-mode harmonic imaging, pulse inversion harmonic imaging, and Doppler harmonic imaging.

Specific Embodiments

Figure 1:
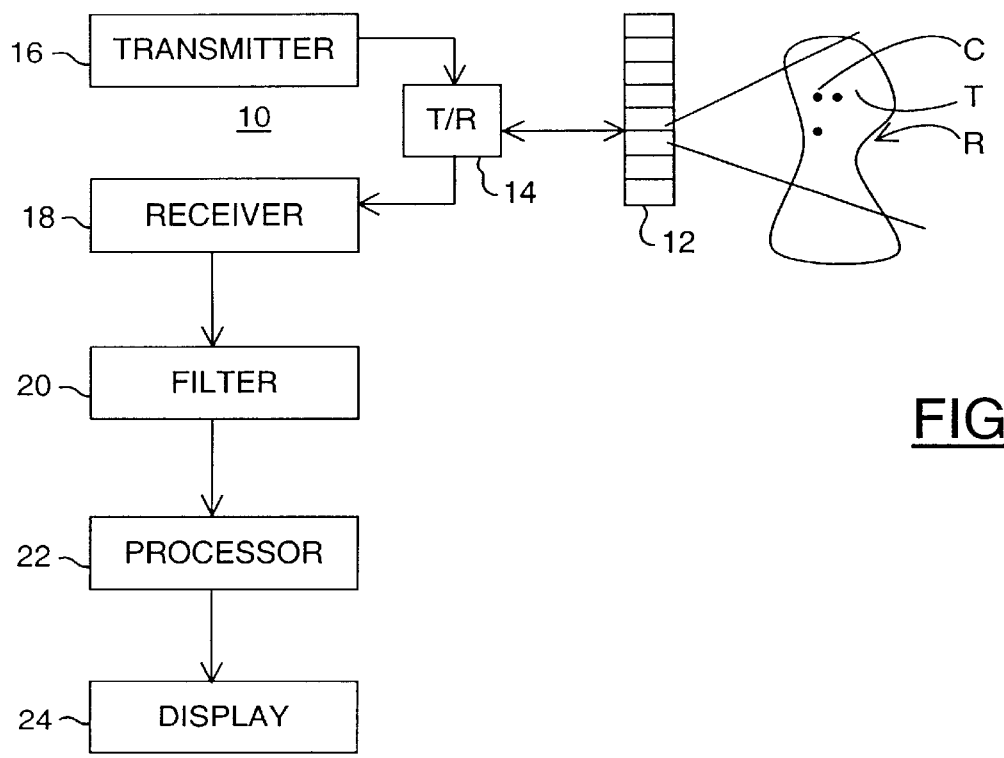
FIG. 1 is a block diagram of an ultrasonic imaging system that incorporates a presently preferred embodiment of this invention.

Turning now to the drawings, FIG. 1 shows a block diagram of a medical diagnostic ultrasonic imaging system 10 that incorporates a preferred embodiment of this invention. The system 10 includes a transducer probe 12 that is coupled via a transmit/receive switch 14 with both a transmitter 16 and receiver 18. Receive signals acquired by the receiver 18 are filtered by a filter 20 and then applied to a processor 22, where the filtered receive signals are processed for display on a display 24.

The transmitter 16 applies transmit signals to the transducer probe 12 to form ultrasonic pulses centered about a fundamental frequency f. These pulses are transmitted into an imaged region R which includes both tissue T and contrast agent C. As used herein, the term "tissue" is intended broadly to encompass organs, blood, bones, and flesh.

Backscattered echoes from the imaged region R impinge upon the transducer probe 12, which generates in response receive signals acquired by the receiver 18. The signal path that includes the receiver 18, the filter 20 and the processor 22 includes a receive beamformer that applies appropriate delays and/or phasings to achieve the desired steering and focusing. The filter 20 is centered between the fundamental frequency f and the second harmonic frequency 2f. This filter can also be used to suppress both the fundamental and harmonic frequency components of the receive signal, retaining only those frequencies in a passband located between the fundamental frequency f and the second harmonic frequency 2f. This can be accomplished by using a narrow band filter for the filter 20 so that only a small region between the fundamental and second harmonic frequencies is passed. Another approach is to design the filter 20 with zeros in the frequency domain at both the fundamental and second harmonic frequencies. Such a filter can readily be implemented using a digital FIR or IIR filter. Filtering can also be done in the analog domain, and depending upon the application the filter 20 can be placed either upstream or downstream of the receive beamformer in the receive processing path.

Figure 2:
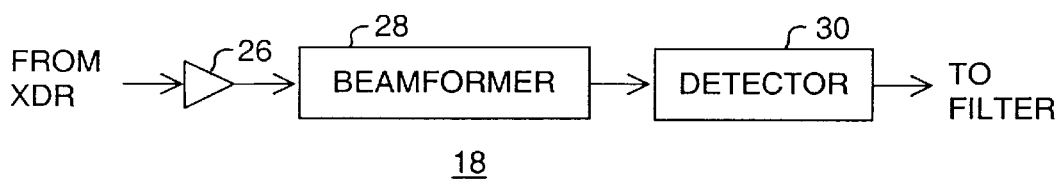
FIG. 2 is a block diagram of a receiver suitable for use in one embodiment of the system of FIG. 1.

FIG. 2 shows one embodiment of the receiver 18. In this embodiment, the receiver 18 includes an amplifier 26, a beamformer 28, and a detector 30. The receiver 18 of FIG. 2 is suited for applications in which the filter 20 is positioned downstream of the beamformer 28.

Figure 3:
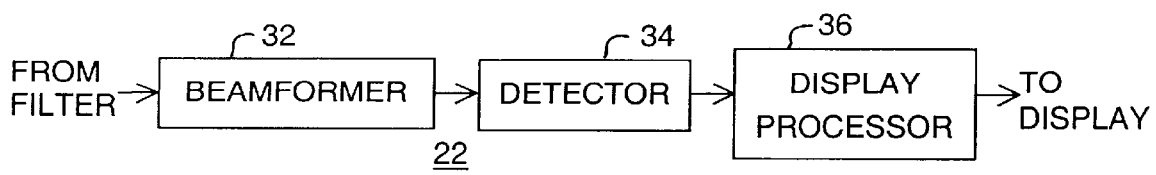
FIG. 3 is a block diagram of a processor suitable for use in another embodiment of the system of FIG. 1.

FIG. 3 shows a processor 22 of another embodiment, in which the beamfomer is positioned downstream of the filter 20. In the embodiment of FIG. 3, the processor 22 includes a beamformer 32, a detector 34, and a display processor 36. The display processor 36 can be any suitable device for harmonic B-mode imaging, two-pulse imaging, harmonic Doppler imaging, harmonic Doppler two-pulse imaging, or the like.

Figure 4:
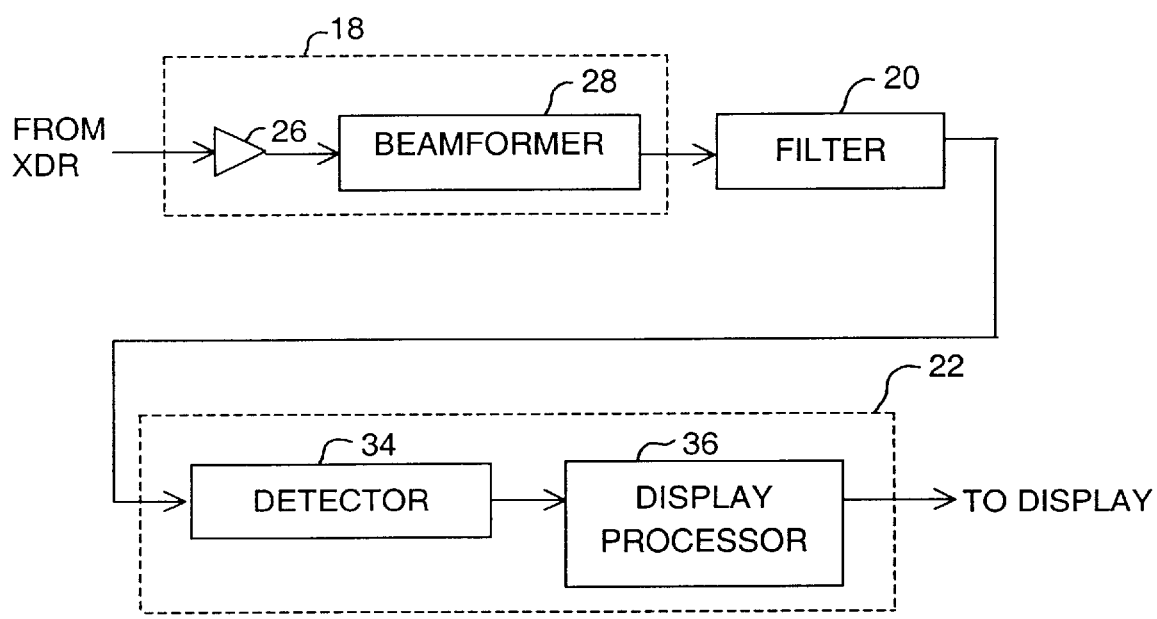
FIG. 4 is a block diagram of a receiver and processor suitable for use in another embodiment of the system of FIG. 1.

FIG. 4 shows a receiver 18 and a processor 22 of another embodiment. In this example, the receiver 18 includes an amplifier 26 and a receive beamformer 28. The processor 22 includes a detector 34 and a display processor 36. As before, any suitable systems can be used for the illustrated components. In some embodiments the filter 20 may be included in the receiver 18.

Figure 5:
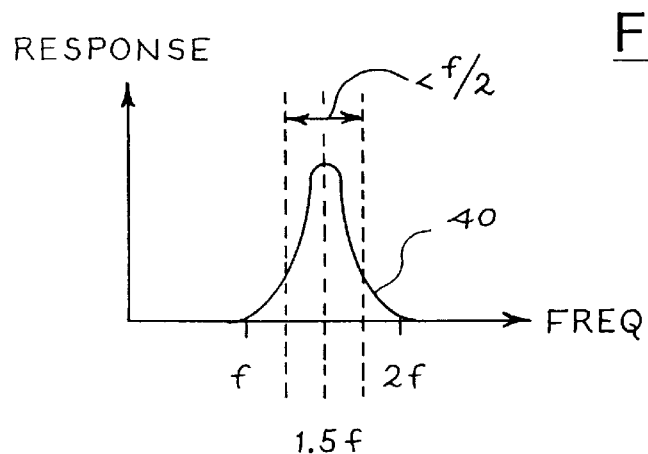
FIG. 5 is a filter response diagram for the filter of FIG. 1.

FIG. 5 shows a filter response that can be used for the filter 20. In FIG. 5, the fundamental frequency f and the harmonic frequency 2f are shown, along with the filter response curve 40. Note that the filter response curve 40 peaks at approximately 1.5 f, and that the filter response curve 40 has a passband (as measured at the −6 db points) approximately equal to f/2.

Figure 6:
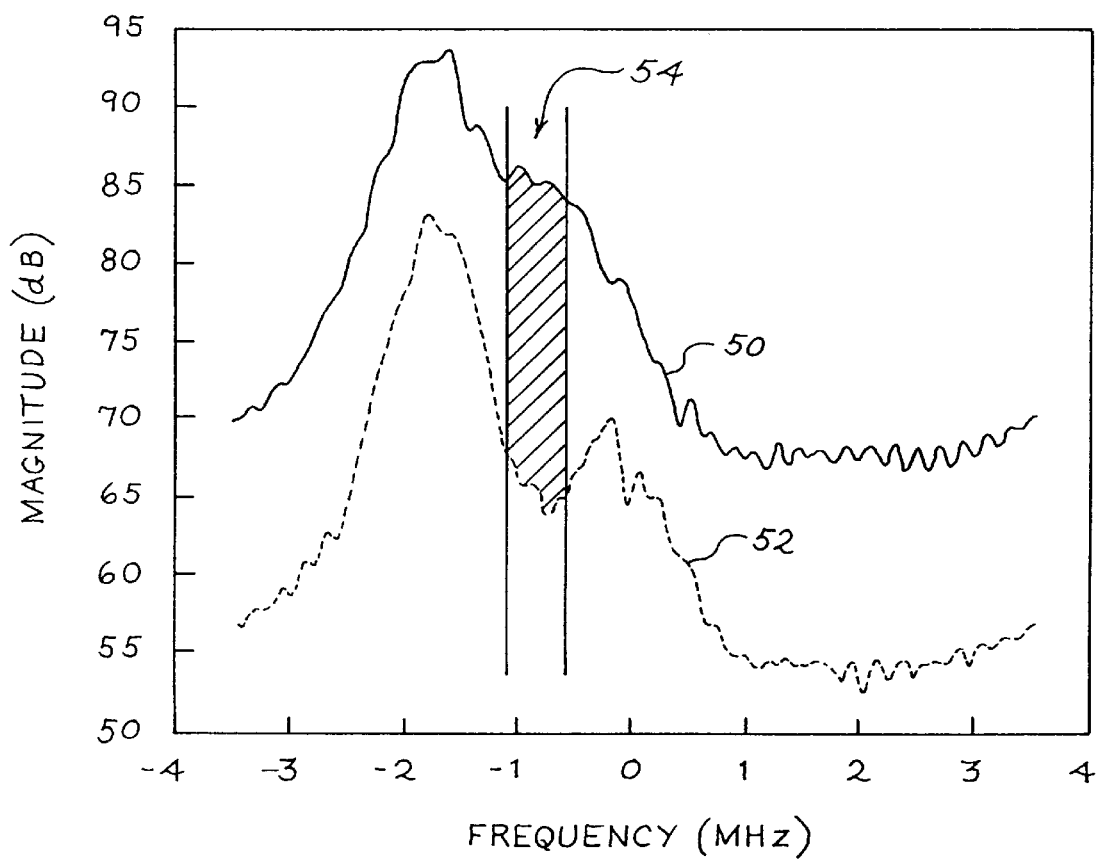
FIG. 6 is a magnitude/frequency diagram illustrating receive signals from contrast agent and tissue.

FIG. 6 is a magnitude/frequency plot that illustrates the differences between unfiltered receive signals from contrast agent (curve 50) and from tissue (curve 52). In FIG. 6 the plotted receive signals have been demodulated to the second harmonic frequency so that 0 MHz corresponds to the second harmonic frequency 2f and −1.75 MHz corresponds to the fundamental frequency f. The spectral response curves of FIG. 6 were acquired using a broadband transmit pulse such as that typically used in tissue harmonic imaging. The curves were obtained from a single pulse at full power with no baseband filter, using the contrast agent distributed under the trade name Optison.

Note that the magnitudes of both curves 50, 52 peak at the fundamental frequency f. In a region 54 between the fundamental frequency f and a second harmonic frequency 2f, the contrast agent curve 50 has a much higher amplitude than the tissue curve 52. In this embodiment, the filter 20 of FIG. 1 has a filter response such as that shown in FIG. 5 that selectively passes frequency components of the receive signals in the region 54. By selectively passing frequency components of the receive signals in the region 54 and suppressing frequency components of the receive signals around both the fundamental and second harmonic frequencies, specificity is improved between contrast agent and tissue.

Figure 7:
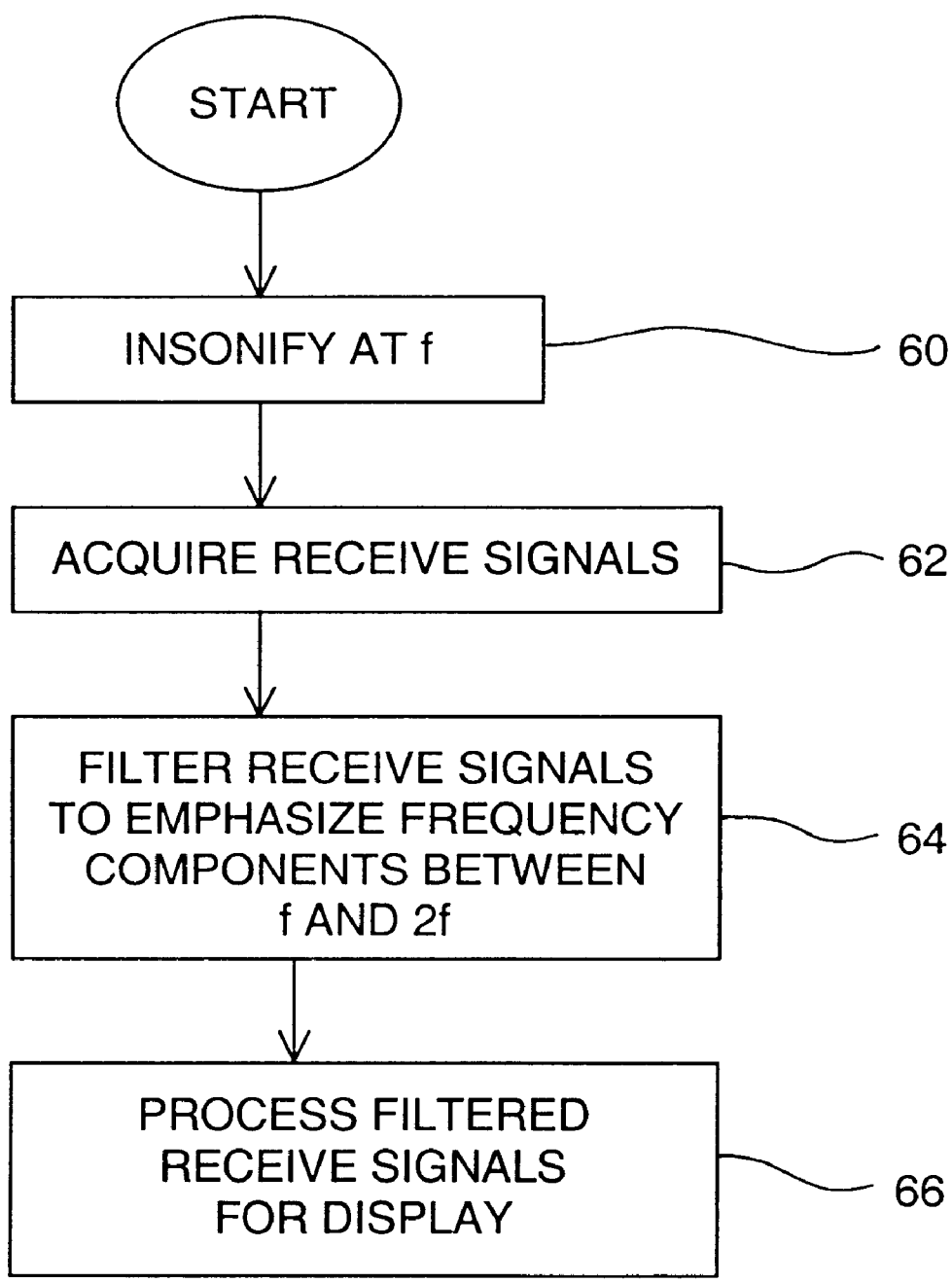
FIG. 7 is a block diagram of a method implemented by the system of FIG. 1.

FIG. 7 is a flow chart illustrating one method performed by the system 10 of FIG. 1. In this method, first the transmitter insonifies a portion of the imaged region in step 60 with an ultrasound pulse having a peak intensity at a fundamental frequency f. In step 62 receive signals are acquired by the receiver, and in step 64 these receive signals are filtered to emphasize frequency components disposed between the fundamental frequency f and the second harmonic frequency 2f. Steps 62 and 64 can be considered as an example of a step for acquiring backscattered ultrasonic receive signals in a passband that peaks at a frequency disposed between nf and (n+1) f, where n is a positive integer. In addition to the filters described above, various other techniques can be used for selectively acquiring backscattered ultrasonic receive signals in the desired passband. For example, demodulation techniques, pulse inversion techniques, and acoustical filters, as well as electronic or digital filters can be used. Thus, backscattered ultrasonic receive signals can be selectively acquired in the desired passband by using a suitable demodulation frequency. Also, pulse inversion techniques well-known to those skilled in the art can be used to selectively suppress fundamental signals in the selectively acquired backscattered receive signals. As yet another example, a transducer can be used which does not efficiently resonate at a harmonic, such as the second harmonic, thereby selectively suppressing second harmonic energy in the selectively acquired receive signals. As used herein, the term "selectively acquiring" is intended broadly to encompass any combination of the methods described above, as well as other methods for ensuring that the receive signals emphasize frequency components in the desired passband while suppressing frequency components in desired regions outside the passband. In step 66 the filtered receive signal is further processed for display.

The improvements described above can be used for B-mode imaging, pulse inversion imaging, power harmonic imaging, or any other imaging method used for contrast agents. When used with pulse inversion and power harmonic imaging, the methods described above have the additional advantage that the effect of tissue motion may be reduced, because tissue motion will appear as signals primarily concentrated at the fundamental and harmonic frequencies, which will be filtered out by the receive filter.

Of course, it should be understood that many changes and modifications can be made to the preferred embodiments described above. For example, any suitable technology can be used for the transmitter 16, the receiver 18, and the transducer probe 12. The transmitter 16 and the receiver 18 can be constructed as digital or analog systems, and the transducer probe 12 can be of any desired type, including 1, 1.5 and 2 dimensional arrays, which are either linear or curved. Mechanically steered transducer elements can be used as well. The filter 20 can be implemented as a digital or analog circuit, and it can be positioned at various points in the receive signal path, either upstream or downstream of the beamformer. Demodulation techniques may also be used to implement the filter 20. The filter can also be implemented as a matched filter, which matches the response of the contrast agent, while treating the response from tissue as well as any noise sources such as electronic noise as a colored noise source. This achieves an optimal filter shape for enhancing signals between the second harmonic and fundamental frequencies. Any suitable technology can be used for the processor 22, which may operate to process the receive signal for display in any desired display mode, including those discussed above.

The preferred embodiment described above has been designed to selectively acquire receive signals in the region between the first harmonic f and the second harmonic 2f. Though this passband is presently preferred, the invention is not limited to this embodiment. In general, this invention can be used to selectively acquire signals in a passband between any two harmonics nf and (n+1) f, where n is a positive integer. For example, the passband can be centered between the second and third harmonics (2$f$ and 3$f$).

Various more complex signal processing techniques can be adapted for use with this invention. For example, a receive signal selectively acquired in a passband between two harmonics as described above can be combined with other signals. As one example, a receive signal selectively acquired in the passband between f and 2f can be combined with another selectively acquired receive signal in a passband between the frequencies 2f and 3f.

As used herein, the term "filter" is intended broadly to include one or more filters. For example, when the filter is positioned downstream of the beamformer, a single filter may be sufficient for an imaging system. Conversely, when the filter is positioned upstream of the beamformer, multiple filters may be used, one associated with each transducer element or group of transducer elements.

The term "receive signal" is intended broadly to encompass signals at any point in the receive processing path between the transducer and the display. Thus, individual analog signals from individual transducer elements as well as digital, beamformed signals are examples of receive signals.

The term "coupled with" is intended broadly to encompass both elements that are coupled directly together and elements that are coupled indirectly together. For example, first and second elements are said to be coupled with one another whether or not intervening elements are placed in the signal path between the first and second elements.

The filter response curves presented above are intended to illustrate preferred embodiments, and not to limit the scope of the invention. Those skilled in the art will recognize that many other filter response curves can be adapted for use with this invention.

The foregoing detailed description has discussed only a few of the many forms that this invention can take. For this reason, this detailed description is intended by way of illustration and not by way of limitation. It is only the following claims, including all equivalents, that are intended to define the scope of this invention.

What is claimed is:

1. A medical diagnostic ultrasound imaging method comprising:
    (a) insonifying a tissue containing a contrast agent with ultrasonic transmit signals at a fundamental frequency f;
    (b) selectively acquiring backscattered ultrasonic receive signals in a passband that peaks at a first frequency disposed between nf and (n+1) f, where n is a positive integer; and
    (c) processing the receive signals for display.

2. The method of claim 1 wherein the passband of (b) substantially blocks components of the receive signals at frequencies nf and (n+1) f.

3. The method of claim 1 wherein the first frequency is substantially equal to (n+½) f.

4. The method of claim 1 or 3 wherein the passband has a width of less than about f/2.

5. The method of claim 1 wherein (a) comprises insonifying the tissue at a power level selected to provide transmit pressures of at least about 100 kPa at a transmit focus.

6. The method of claim 1 wherein (c) comprises processing the receive signals for display in an imaging mode selected from the group consisting of: B-mode harmonic imaging, pulse inversion imaging, and color harmonic imaging.

7. The method of claim 1 wherein (b) comprises filtering the receive signals with a filter selected from the group consisting of: an FIR filter, an IIR filter, a matched filter, and an analog filter.

8. The method of claim 1 where n=1.

9. The method of claim 8 wherein the passband of (b) substantially blocks components of the receive signals at frequencies f and 2f.

10. The method of claim 8 wherein the first frequency is substantially equal to 1.5 f.

11. The method of claim 8 or claim 10 wherein the passband has a width of less than about f/2.

12. A medical diagnostic ultrasound imaging system comprising:

at least one transducer probe;

a transmitter coupled to the at least one transducer probe and operative to insonify a tissue containing a contrast agent with ultrasonic transmit signals at a fundamental frequency f;

a receiver coupled to the at least one transducer probe and operative to selectively acquire ultrasonic receive signals from the tissue and the contrast agent in a passband that peaks at a first frequency disposed between nf and (n+1) f, where n is a positive integer; and a processor coupled with the receiver and operative to process the receive signals for display.

13. The invention of claim 12 wherein the passband substantially blocks components of the receive signals at frequencies nf and (n+1) f.

14. The invention of claim 12 wherein the first frequency is substantially equal to (n+½) f.

15. The method of claim 12 or claim 14 wherein the passband has a width of less than about f/2.

16. The invention of claim 12 wherein the transmitter is operative to insonify the tissue at a power level selected to provide transmit pressures of at least about 100 kPa at a focus.

17. The invention of claim 12 wherein the processor is operative to process the receive signals for display in an imaging mode selected from the group consisting of: B-mode harmonic imaging, pulse inversion imaging, and color harmonic imaging.

18. The invention of claim 12 wherein the receiver comprises a filter selected from the group consisting of: an FIR filter, an IIR filter, a matched filter, and an analog filter.

19. The invention of claim 12 wherein n=1.

20. The invention of claim 19 wherein the passband substantially blocks components of the receive signals at frequencies f and 2f.

21. The invention of claim 19 wherein the first frequency is substantially equal to 1.5 f.

22. The invention of claim 19 or 21 wherein the passband has a width of less than about f/2.

* * * * *